United States Patent
Bonnet et al.

(10) Patent No.: US 9,782,117 B2
(45) Date of Patent: Oct. 10, 2017

(54) SYSTEM WITH KINESTHETIC STIMULATION MEDICAL DEVICE FOR THE NON-INVASIVE ASSESSMENT OF THE SYMPATHOVAGAL BALANCE OF A PATIENT

(71) Applicants: SORIN CRM SAS, Clamart (FR); UNIVERSITÉ DE RENNES 1, Rennes (FR)

(72) Inventors: Jean-Luc Bonnet, Massy (FR); Alfredo Hernandez, Cesson Sévigné (FR)

(73) Assignees: SORIN CRM SAS, Clamart (FR); UNIVERSITÉ DE RENNES 1, Rennes (FR)

( * ) Notice: Subject to any disclaimer, the term of this patent is extended or adjusted under 35 U.S.C. 154(b) by 47 days.

(21) Appl. No.: 14/617,555

(22) Filed: Feb. 9, 2015

(65) Prior Publication Data
US 2015/0223746 A1    Aug. 13, 2015

(30) Foreign Application Priority Data
Feb. 11, 2014    (FR) ...................................... 14 00374

(51) Int. Cl.
*A61B 5/04*    (2006.01)
*A61B 5/00*    (2006.01)
(Continued)

(52) U.S. Cl.
CPC .......... *A61B 5/4076* (2013.01); *A61B 5/0051* (2013.01); *A61B 5/024* (2013.01);
(Continued)

(58) Field of Classification Search
None
See application file for complete search history.

(56) References Cited

U.S. PATENT DOCUMENTS

2007/0167851 A1*   7/2007   Vitali ................... A61B 5/0816
                                                                    600/513
2007/0239210 A1   10/2007   Libbus et al.
(Continued)

FOREIGN PATENT DOCUMENTS

EP         1 741 387        1/2007

OTHER PUBLICATIONS

Goldberger, JJ. "Sympathovagal balance: how should we measure it?" Am J Physiol. Apr. 1999;276(4 Pt 2):H1273-80.*
(Continued)

*Primary Examiner* — Ankit D Tejani
(74) *Attorney, Agent, or Firm* — Foley & Lardner LLP

(57) ABSTRACT

A system for assessing a sympathovagal balance of a patient includes a generator configured to produce stimulation pulses, a stimulator that receives the stimulation pulses produced by the generator and outputs a stimulation energy, a sensor configured to measure a physiological signal, and a processor. The processor is configured to control the generator during a plurality of sequences to produce the stimulation pulses over a test period, determine a biological parameter of a current activity of the patient derived from the physiological signal, determine a variation of the biological parameter resulting from the stimulation pulses, and determine a sympathovagal balance index according to the variation in the biological parameter.

12 Claims, 4 Drawing Sheets

(51) Int. Cl.
 A61B 5/024    (2006.01)
 A61B 5/0452   (2006.01)
 A61B 5/0205   (2006.01)
 A61B 5/0402   (2006.01)
 A61B 5/08     (2006.01)
 A61B 5/1455   (2006.01)
 A61B 7/04     (2006.01)

(52) U.S. Cl.
 CPC ........ *A61B 5/0205* (2013.01); *A61B 5/02405* (2013.01); *A61B 5/0402* (2013.01); *A61B 5/0452* (2013.01); *A61B 5/08* (2013.01); *A61B 5/14552* (2013.01); *A61B 5/4035* (2013.01); *A61B 5/7275* (2013.01); *A61B 7/04* (2013.01)

(56) References Cited

U.S. PATENT DOCUMENTS

| | | | |
|---|---|---|---|
| 2008/0281372 A1 | 11/2008 | Libbus et al. | |
| 2010/0268104 A1 | 10/2010 | Lee et al. | |
| 2013/0123873 A1* | 5/2013 | Libbus ............... | A61N 1/36114 607/18 |
| 2013/0268030 A1* | 10/2013 | Lee .................... | A61B 5/08 607/62 |

OTHER PUBLICATIONS

Preliminary Search Report for French Patent Application No. FR 1400374, dated Oct. 7, 2014, 2 pages.

* cited by examiner

SYSTEM WITH KINESTHETIC STIMULATION MEDICAL DEVICE FOR THE NON-INVASIVE ASSESSMENT OF THE SYMPATHOVAGAL BALANCE OF A PATIENT

CROSS REFERENCE TO RELATED APPLICATIONS

This application claims the benefit of and priority to French Patent Application No. 14/00374, filed Feb. 11, 2014, which is hereby incorporated by reference herein in its entirety.

BACKGROUND

The cardiovascular system is under the control of both the sympathetic and the parasympathetic system. In a normal patient, these two systems are balanced, which results in particular in a heartbeat well suited to the patient's current activity (Chronotropic effect), satisfactory cardiac contractility (inotropic effect), etc. Sympathovagal balance or SVB is the balance between the sympathetic and parasympathetic branches of the autonomic nervous system. SVB may play an important role in a number of pathologies such as heart failure or myocardial infarction. The evaluation of SVB can be an important tool for the diagnosis, monitoring, and selection of a therapy for pathologies of this type.

In a patient with heart failure, or with post-myocardial infarction, sympathetic activity is excessive (hypertonic sympathetic state), compared to a depressed parasympathetic system, which leads to an abnormally faster heart rate. The sympathovagal balance is nevertheless difficult to determine, especially in acute crisis situations or in the presence of a chronic evolution of disease. The sympathovagal balance may be evaluated at regular intervals, for example daily, with an external or implantable device providing continuous monitoring of the patient.

The conventional method of assessing the situation of the autonomic nervous system of a patient, and thus its sympathovagal balance, is often based on the analysis of indicators of Heart Rate Variability (HRV) in the frequency or time domain. The evaluation of the sympathovagal balance may be based on the application of "autonomic maneuvers" which trigger a response from the patient's autonomic nervous system ("autonomic response").

Autonomic maneuvers may implement pharmacological or mechanical manipulation (e.g., a Valsalva maneuver, a tilt test, etc.) to create a controlled modification of the cardiovascular system designed to provoke a response of the autonomic nervous system, which is collected and analyzed. A direct evaluation of the activity of the autonomic nervous system may also be made in the brain, but with highly invasive techniques. These various maneuvers cannot be applied in the context of regular monitoring of a patient with an implantable or ambulatory system, as this would involve asking the patient to repeatedly and reproducibly perform these autonomous maneuvers. Additionally, the maneuvers are often not possible because of the patient's medical condition, or even more during sleep (which is the most favorable period for assessing the sympathovagal balance given the minimum impact of external factors).

Various methods, such as the one disclosed by US2008/0281372 A1, have been proposed to analyze the HRV after spontaneous or induced disturbances of the cardiovascular system without the patient's active participation. In particular, the analysis of Heart Rate Turbulence (HRT) may be used as a disturbance to the occurrence of spontaneous ectopic beat. Although this method can be easily applied to an implantable system for regular monitoring of the sympathovagal balance, it is based on unpredictable events (e.g., ectopic beats, etc.), which may occur at random times, or not at all, causing significant bias in the estimation of sympathovagal balance. Other methods may apply a ventricular stimulation to reproduce the ectopic event used as cardiovascular disturbance for the analysis of the autonomic response. This solution, based on the production of an ectopic beat, is however deleterious especially for heart failure patients.

In any event, these techniques presuppose the existence of an implantable device in the patient (cardiac or similar pacemaker), which greatly reduces the patient population to which they may be applied. The need therefore remains to have an external, noninvasive device to assess the balance of any patient, for example using a Holter-type recorder, requiring no intervention other than the installation of electrodes, sensors, or other transducers on the body of the patient and their connection to a device ambulatory worn by the latter.

In this regard, techniques have been proposed that are not based on the patient's heart rhythm. These include analysis of the variability in blood pressure or in the cardiac contractility, when such information is available. But in these proposals, it is always necessary to cause reproducible autonomous maneuvers to obtain reliable estimates of the evolution of sympathovagal balance. The need thus remains to have a system to fully automatically and noninvasively assess the sympathovagal balance without any patient or caregiver involvement. It would be particularly advantageous for that purpose to have a device that is compatible with a long duration clinical follow-up or monitoring. For example by delivering a daily index or indicator representative of the sympathovagal balance of the patient from cardiovascular signals collected by the device in response to a controlled, reproducible, and not deleterious modification to the patient's autonomic nervous system.

US 2010/0268104 A1 discloses such a device that stimulates the auditory system of the patient through an acoustic transducer emitting in the ear of the patient more or less high and more or less strong tones. As well as simultaneously collecting an electrocardiogram which is analyzed to assess HRV variability. Instead, a device of a different type is contemplated, based on the use of a kinesthetic effector including a vibrator placed against the patient's skin. The vibrator produces a vibrating mechanical stimulation on the skin which is detected by the sensory receptors or mechanoreceptors in the body and transmitted to the autonomous central nervous system via the sensory nerves.

SUMMARY

According to an exemplary embodiment, a system including an active medical device, includes:
  A generator capable of producing kinesthetic stimulation controlled pulse bursts;
  At least a kinesthetic effector adapted to be applied to a patient's outer skin site, and including a vibrating electromechanical transducer adapted to receive the pulses produced by the generator and to deliver a given kinesthetic stimulation energy; and
  Methods for collecting at least one physiological signal representative of cardiac activity.

According to various embodiments, the active medical device further includes:

Controlled activation methods of the generator at programmed intervals for production for a predetermined test period of kinesthetic stimulation bursts;

Methods for measuring, for each burst of kinesthetic stimulation, at least one control parameter of the patient's current autonomic activity, derived from the at least one received physiological signal;

Calculating methods of the variation of at least one control parameter resulting of the kinesthetic stimulation, this variation being calculated from values of said at least one control parameter, including at least two values from the group including:
  i) a base value measured for a steady period anterior to the production of the kinesthetic stimulation pulse burst;
  ii) a current value measured during a production period of the kinesthetic stimulation pulse burst; and
  iii) a current value measured during a subsequent recovery period of the production of the kinesthetic stimulation pulse burst; and Evaluator methods able to determine an SVB index for changes in the at least one control parameter resulting from kinesthetic stimulation, calculated during said predetermined test period.

According to an exemplary embodiment:

During the test period, the generator produces a plurality n of kinesthetic stimulation pulse bursts;

During a period including said recovery period, the measuring methods may be adapted to measure the current value of the at least one control parameter in synchronization with the patient's heart rate during a plurality of successive cardiac cycles, for each individual burst of n discrete samples of the at least one respective control parameter of rank i, with i=1 ... n; and The evaluators methods may be able to calculate an average of n samples of the same rank i of at least one control parameter for the same test period, thus giving n averaged parameter values of the control parameter, all these n averaged values being the SVB index of the test period.

The system may further include methods adapted to inhibit the controlled activation methods of the generator in the event of detection by the device of the occurrence of at least one event among the group including: heart rate below a predetermined threshold, presence of a physical activity of the patient, delivery of a cardiac stimulation, presence of an apnea or hypopnea episode, and presence of an arrhythmia episode.

The indicator of the current autonomic activity parameter of the patient may be especially at least one of the group including: the RR interval as a chronotropic parameter; PR interval as a dromotropic parameter; and an endocardial acceleration parameter as an inotropic parameter.

One embodiment relates to a system for assessing a sympathovagal balance of a patient. The system includes a generator configured to produce stimulation pulses, a stimulator that receives the stimulation pulses produced by the generator and outputs a stimulation energy, a sensor configured to measure a physiological signal, and a processor. The processor is configured to control the generator during a plurality of sequences to produce the stimulation pulses over a test period, determine a biological parameter of a current activity of the patient derived from the physiological signal, determine a variation of the biological parameter resulting from the stimulation pulses, and determine a sympathovagal balance index according to the variation in the biological parameter.

According to an exemplary embodiment, the physiological signal includes at least one of a cardiac activity, an ECG, a heart rate, breathing, an oxygen saturation, a pulse wave, and a phonocardiogram. The biological parameter of the current activity of the patient includes at least one of a RR interval as a chronotropic parameter, a PR interval as a dromotropic parameter, and an endocardial acceleration as an inotropic parameter.

In one embodiment, the variation of the biological parameter is determined from at least two values for each sequence of the test period. The at least two values for each sequence may include (i) a base value measured for a baseline period prior to the production of the stimulation pulses; (ii) a current value measured during an ANS period of production of the stimulation pulses; and (iii) a current value measured for a recovery period during which the stimulation pulses are stopped. According to various embodiments, the generator produces a plurality of stimulation pulses during the ANS period. Each of the plurality of simulation pulses includes a rank i, such that the rank i ranges from 1 to n for each sequence. In one embodiment, the processor determines the current value of the biological parameter in synchronization with the cardiac rhythm of the patient during a plurality of successive cardiac cycles during the recovery period.

In various embodiments, each of the plurality of the simulation pulses corresponds with one of a plurality of samples of the biological parameter. The processor may calculate an average of the plurality of samples of the biological parameter of the same rank i over all sequences of the test period, resulting in n averaged values of the biological parameter. The n averaged values of the biological parameter are the sympathovagal balance index of the test period. In some embodiments, the sympathovagal balance index is calculated during the test period.

According to an exemplary embodiment, the processor inhibits the generator upon detection of the occurrence of at least one of a heart rate below a predetermined threshold, a presence of a patient's physical activity, a cardiac stimulation delivery, a presence of an apnea or hypopnea episode, and a presence of an arrhythmia episode.

Another embodiment relates to a method for assessing a sympathovagal balance of a patient. The method includes acquiring, by a sensor, a physiological signal; controlling, by a processor, a generator configured to produce stimulation pulses during a plurality of sequences over a test period; determining, by the processor, a biological parameter of a current activity of the patient derived from the physiological signal; determining, by the processor, a variation of the biological parameter resulting from the stimulation pulses; and determining, by the processor, a sympathovagal balance index according to the variation in the biological parameter.

According to an exemplary embodiment, the physiological signal includes at least one of a cardiac activity, an ECG, a heart rate, breathing, an oxygen saturation, a pulse wave, and a phonocardiogram. The biological parameter of the current activity of the patient includes at least one of a RR interval as a chronotropic parameter, a PR interval as a dromotropic parameter, and an endocardial acceleration as an inotropic parameter.

In one embodiment, the variation of the biological parameter is determined from at least two values for each sequence of the test period. The at least two values for each sequence may include (i) a base value measured for a baseline period prior to the production of the stimulation pulses; (ii) a current value measured during an ANS period of production of the stimulation pulses; and (iii) a current value measured for a recovery period during which the stimulation pulses are stopped.

In some embodiments, the method further includes producing, by the generator, a plurality of stimulation pulses during the ANS period. Each of the plurality of simulation pulses includes a rank i, such that the rank i ranges from 1 to n for each sequence. In one embodiment, the method further includes determining, by the processor, the current value of the biological parameter in synchronization with the cardiac rhythm of the patient during a plurality of successive cardiac cycles during the recovery period. In another embodiment, the method further includes calculating, by the processor, an average of a plurality of samples of the biological parameter of the same rank i over all sequences of the test period, resulting in n averaged values of the biological parameter. Each of the plurality of the simulation pulses corresponds with one of the plurality of samples of the biological parameter. The n averaged values of the biological parameter are the sympathovagal balance index of the test period. According to an exemplary embodiment, the sympathovagal balance index is calculated during the test period.

In one embodiment, the method further includes inhibiting, by the processor, the generator upon detection of the occurrence of at least one of a heart rate below a predetermined threshold, a presence of a patient's physical activity, a cardiac stimulation delivery, a presence of an apnea or hypopnea episode, and a presence of an arrhythmia episode.

Still another embodiment relates to a device for assessing a sympathovagal balance of a patient. The device includes a generator configured to produce stimulation pulses, a stimulator that receives the stimulation pulses produced by the generator and outputs a stimulation energy, a sensor configured to measure a physiological signal, and a processor configured to determine a sympathovagal balance index according to a variation in a biological parameter based on the physiological signal over a time period.

DESCRIPTION OF THE FIGURES

Further features, characteristics and advantages of the present invention will become apparent to a person of ordinary skill in the art from the following detailed description of preferred embodiments of the present invention, made with reference to the drawings annexed, in which like reference characters refer to like elements and in which:

FIG. 4 also shows the average response of the RR cycles consecutive to kinesthetic stimuli of different amplitudes on a healthy subject, with the different phases of the response, according to an exemplary embodiment.

DETAILED DESCRIPTION

Figure 1:
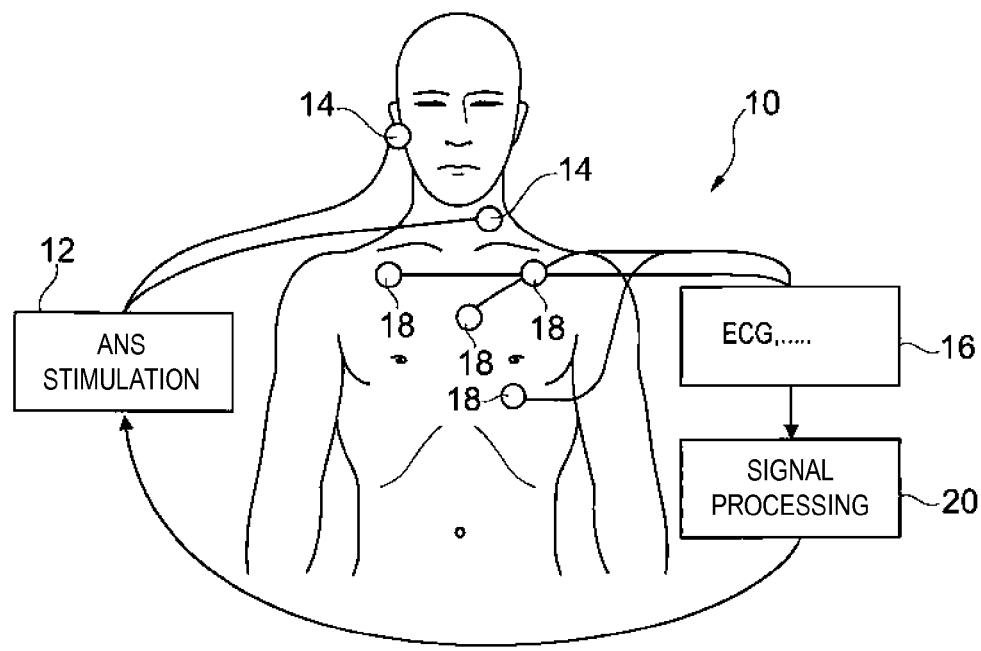
FIG. 1 is a schematic representation of the different elements of the system for assessment of the sympathovagal balance, according to an exemplary embodiment.

Referring now to FIG. 1, numeral reference 10 generally designates the system of the invention for the assessment of the sympathovagal balance (SVB) of a patient. As shown in FIG. 1, the system 10 includes a stimulation device with a generator housing 12 producing pulses applied to one (or more) effector(s) 14. In one embodiment, the effector 14 includes, for example, a vibrator disposed in/on a sensitive region of the skin. In some embodiments, the vibrator is disposed in the region of the mastoid bone in the vicinity of the ear. In other embodiments, the effector 14 is, for example, a transducer of the type C10-100 of Precision Microdrives or C2 Tactor of Engineering Acoustics. The type of transducer is a transducer that weighs a few grams. The transducer is capable of emitting vibrations through an integrated vibrator excited by pulse trains of varying amplitude and duration, typically at a frequency of 250 Hz which is the resonance nominal frequency of the effector 14 and which is also the frequency at which the skin mechanoreceptors are the most sensitive. Other types of effectors may of course effectively be used.

Vibrotactile stimulation applied to the skin by the effector 14 may be detected by the sensory receptors or mechanoreceptors in the body. The sensory receptors or mechanoreceptors may forward the vibrotactile stimulation to the autonomous central nervous system via the sensory nerves. This type of dermal operated vibrotactile stimulation may generate a controlled disruption of the autonomic system, and is herein designated as "kinesthetic stimulation" or "ANS stimulation" (Autonomic Nervous Stimulation).

The generator 12 is controlled by a microcontroller and has methods for adjusting the intensity (that is to say, energy) of kinesthetic stimulation. The intensity may be adjusted by controlled variation of the amplitude and/or the number, the duration, and/or the frequency of the pacing pulse trains forming the signal applied to the effector 14. The system 10 also includes a Holter recorder device with an acquisition module 16 for acquiring data from various sensors or electrodes 18 that measure physiological signals such as the ECG, the heart rate, the breathing, the oxygen saturation, the pulse wave, the phonocardiogram, etc. As is described more fully herein, the methods focus on physiological signals directly related to cardiac activity, including heart rate, which is a parameter that may be obtained from an ECG signal. However, this is not restrictive as the methods may be implemented using other physiological signals non-invasively collected on/from the patient's body.

In particular, the myocardium endocardial acceleration (EA) is a signal that may provide various significant parameters reflecting the activity of the heart. The EA signal may be obtained by external methods such as an accelerometer collecting a phonocardiographic signal. It may for example be referred to in EP 1741387 A1 (Sorin CRM S.A.S., previously ELA Medical), which describes an apparatus for non-invasively collecting and processing such signals in a patient. In particular, the method may extract various representative parameters such as the peak amplitude of the endocardial acceleration (PEA), the time interval between the two peaks PEA1 and PEA2 corresponding to the two major heart sounds, etc. Others signals may be collected including the acquisition of surface biopotentials such as ECG, ENG, EEG, and EMG (respectively cardiac, nervous, encephalographic, and muscular potentials).

The acquisition module 16 includes all components necessary for the amplification and filtering of the collected physiological signals. The physiological signals are then applied to a signal processing module 20 for extracting, as is discussed more fully herein, a set of specific parameters bearing information representative of the SVB balance. The physiological signals may provide information on the effect of the autonomic perturbation of kinesthetic stimulation on the cardiovascular system. The signal processing module 20 is also coupled to the generator 12 so as to adjust a number of operating parameters thereof, especially the moment of issuance of a pulse burst. The ECG signals collected by the acquisition module 16 thus control the generator 12 so that it may deliver ANS pulse bursts to the effector 14 at the most appropriate moment of the cardiac depolarization wave. In one embodiment, the Holter recorder device of the acquisition module 16 may also include wired or wireless coupling methods to an external device, such as a programmer for collecting data in a record. In other embodiments, the Holter recorder may be coupled to a home monitoring system to collect patient data at regular intervals and transmit the data to a remote center for offline analysis.

Figure 2:
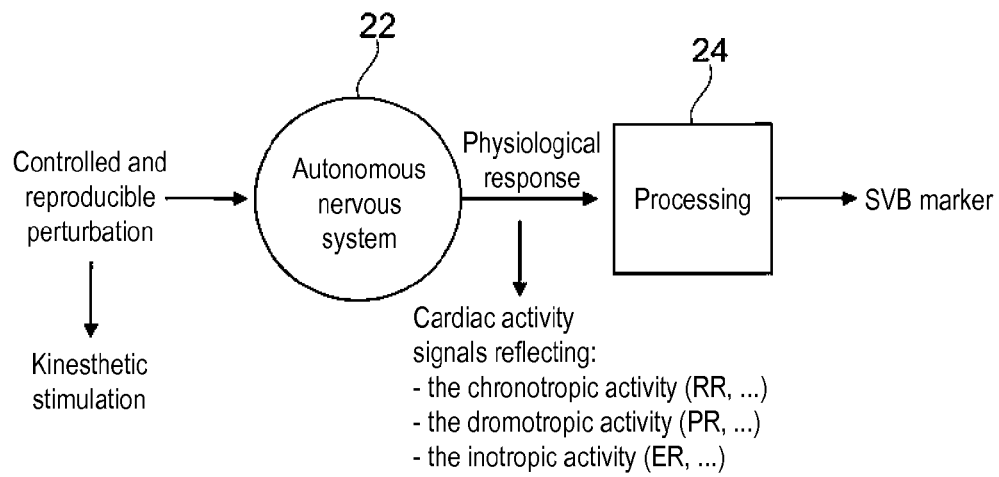
FIG. 2 is a schematic representation of the principle on which the system for the assessment of sympathovagal balance is based, according to an exemplary embodiment.

Referring now to FIG. 2, FIG. 2 illustrates a schematic representation of the principle on which the system 10 for the assessment of sympathovagal balance is based. The system 10 generates controlled and reproducible changes in the autonomous nervous system 22 through, for example, sympathetic stimulation such as kinesthetic stimulation (ANS), to assess the sympathovagal balance of the patient. Such changes applied to the autonomous nervous system 22 produces a physiological response measured on a number of signals. The collected signals are processed by processor 24 to obtain a reliable indicator or marker of sympathovagal balance state of the patient and of the evolution of the balance in time.

According to an exemplary embodiment, to apply the controlled modification to the autonomous nervous system 22 at a given moment, a pacing algorithm is initiated. The pacing algorithm may be predefined within the system 10 or determined by the system 10 during the test period. The pacing algorithm produces an ANS pulse sequence, described in more detail with reference to FIGS. 3 and 4 below. A sympathetic ANS stimulation (such as that produced by a kinesthetic stimulation) produces a number of effects on cardiac activity, which may include:

Chronotropic effect: increase in heart rate, reduction of RR intervals;
Dromotropic effect: increase in AV conduction velocity, leading to a decrease in PR intervals;
Bathmotropic effect: increased excitability of the myositis;
Inotropic effect: increased cardiac contractility; and/or
Lusitropic effect: decrease in heart relaxation speed.

ANS stimulation may also have an effect on the vascular system by modulation of vasoconstriction, with a modification of the diameters of the arteries and of the peripheral resistance resulting in a general vasoconstriction of the vascular system. The opposite effects are generally produced by parasympathetic (vagal) stimulation.

Figure 3:
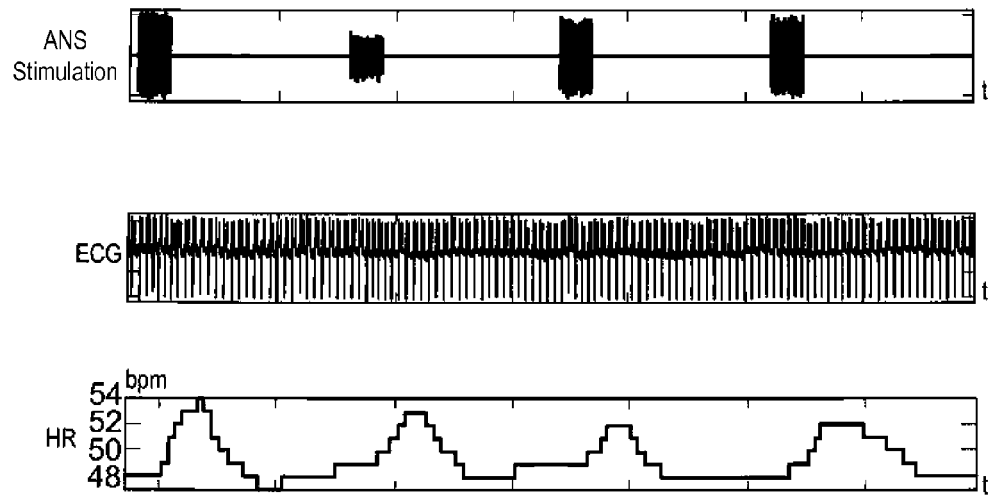
FIG. 3 is an example of cardiac activity signals recorded in a patient during the delivery of kinesthetic stimulation bursts (vibrotactile stimulation), according to an exemplary embodiment.

FIG. 3 shows an example of cardiac activity signals (ECG electrocardiogram and heart rate HR) recorded in a patient paired with equipment such as the system 10 of FIG. 1, during delivery of ANS stimulation bursts (timing diagram referenced "Stim ANS"). The ANS stimulation, in this example, includes a sequence of four bursts of different amplitudes. Each burst includes a stimulation duration of 5 s at a fixed frequency of 250 Hz and "white" periods of 30 s separating each of these bursts. As shown in FIG. 3, the stimulation is carried out asynchronously with respect to the cardiac rhythm. The positive chronotropic effect generated by the vibrotactile stimulation (with sympathetic predominance) is clearly visible on the HR signal, each stimuli causing an increase in the heart rate of several beats per minute (bpm).

In general, the chronotropic response of the heart rhythm to sympathetic ANS stimulation may be separated into four phases (reflected by the change in RR interval). These phases are particularly visible in FIG. 4, which shows the average response of RR cycles following kinesthetic stimuli of different amplitudes on a healthy subject. The typical shape of the chronotropic response to this type of stimulation includes four distinct phases:

Phase 1: reduction of the RR interval (increased HR signal);
Phase 2: pseudo-plateau phase, with more or less a visible increase in RR intervals;
Phase 3: rapid increase in RR interval;
Phase 4: "bounce" phase, which reflects the baroreflex transient responses, involving both the sympathetic and parasympathetic systems and leading to a final stabilization of blood pressure and heart rate.

Figure 4:
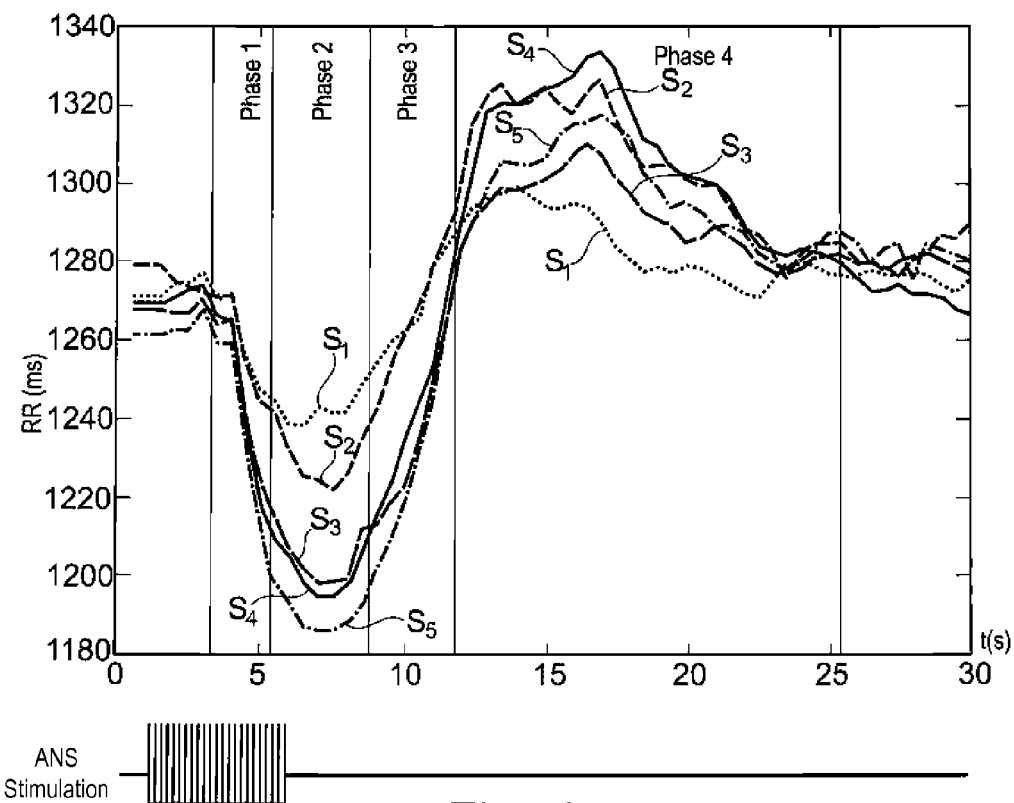
FIG. 4 illustrates an example of kinesthetic stimulation bursts used for the implementation of the assessment of sympathovagal balance, according to an exemplary embodiment.

FIG. 4 also shows a "dose-response" effect. For example, the greater the stimulation amplitude, the higher the peak-to-peak amplitude and therefore the higher the slope of the response is (S1-S5 responses corresponding to stimulations of respective increasing magnitudes). Note also that the phase shift between the beginning of the ANS stimulation and the beginning of the chronotropic response is variable between individuals. The four phases 1-4 above may also be observed on the inotropic response (variation of cardiac contractility) or on the other types of response, but with slower dynamics due to larger time constants. For this reason, it is preferable to choose—but not be limited—to analyze the heart rate (RR intervals) to evaluate the sympathovagal balance of the patient, according to an exemplary embodiment.

ANS stimulation may be defined by many configuration parameters such as:

Synchronism: ANS stimulation may be synchronous to cardiac events (as in the present example), or desynchronized thereof;
In the case of a synchronous stimulation, the ratio between ANS stimulation and cardiac events (e.g., a ratio of 1:1 indicating an ANS stimulation for each detected cardiac event, a ratio of 1:4 indicating an ANS stimulation pulse every four heart events, etc.);
In the case of an ANS synchronous pacing, R-ANS interval; this parameter describing the delay between the detection of the cardiac event and the start of the ANS pulse burst;
Effective voltage (RMS) (or amplitude) issued to the kinesthetic effector;
ANS stimulation frequency of each burst;
Inter-burst frequency;

Pulse width;

Number of repetitions of the pulse sequence; and

Duty cycle representing the alternating periods of stimulation and no stimulation.

According to the exemplary embodiment shown in FIG. 3, the ANS stimulation includes asynchronous stimuli with a 250 Hz stimulation frequency (close to the optimum frequency response of mechanoreceptors), a duration of 5 s, a 30 second inter-burst duration, and of variable amplitude.

Figures 5, 6:
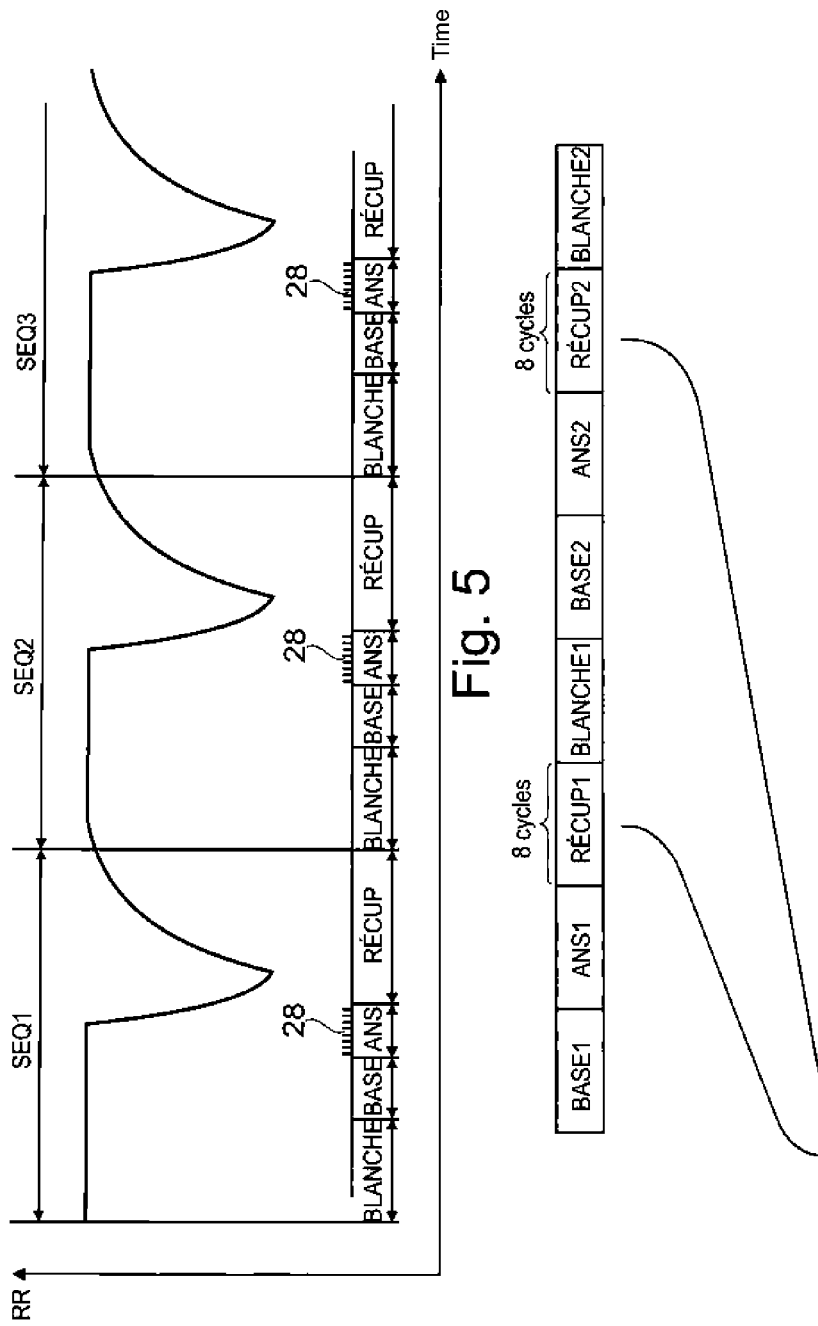
FIG. 5 illustrates the variations of the RR distances in response to the bursts application such as those of FIG. 4, during three successive sequences of a test period, according to an exemplary embodiment.
FIG. 6 shows the method of collection, storage, and averaging of the heart rate data, in order to assess the patient's physiological condition, according to an exemplary embodiment.

FIG. 5 illustrates the succession of analysis sequences of the variations of heart rate (assessed by measurement of RR interval) in response to the successive ANS bursts 28. Each of these sequences (SEQ1, SEQ2, . . . ) includes:

A white period (BLANCHE) allowing the autonomic nervous system to return to its initial state after the change resulting from the ANS stimulation from the previous sequence. During the white period, the ANS stimulation is disabled;

A "baseline" period (BASE) for recording a steady state of cardiac activity signals just before application of the ANS stimulation. During the baseline period, the system may also check if a number of criteria are met, corresponding to a patient's condition allowing a representative recording of his/her clinical condition: sufficiently high heart rate, lack of exercise, lack of apnea or hypopnea phase, no arrhythmias, etc. This list is not exhaustive. If one of these criteria is not verified, the following analysis is inhibited, otherwise it is continued;

A period of delivery of controlled stimulation (ANS); and

A recovery period (RÉCUP), during which ANS stimulation is stopped.

Heart rate (RR intervals) is measured during at least one of the baseline period (BASE), the period of delivery of controlled stimulation (ANS), and the recovery period (RÉCUP). In particular, the information gathered during the recovery period, just after the production of the ANS burst, may be used to evaluate the sympathovagal balance of the patient, once the information has been processed. The signals measured in the different periods may be integrally or independently processed. A first example of such processing to obtain a SVB index from an analysis of the single recovery period is described hereinafter. Heart rate (RR intervals) is measured at each recovery period RÉCUP1, RÉCUP2, etc. during eight cardiac cycles, for example. Thus, giving eight samples for each cycle that are stored as a vector {RR11, RR12, . . . RR18}. The vector includes eight ordered values for measurements made during the RÉCUP1 recovery phase of the first sequence SEQ1, and so on for the following sequences SEQ2, SEQ3, etc.

Upon completion of the SEQ1, SEQ2, . . . , SEQN series of over the test period, all samples of the same rank which have been stored are averaged, giving a score of eight values {RRm1, RRm2, . . . RRm8}. The score of eight values describe, in averaged form, the profile of the curve of variation of the RR interval during the recovery phase. FIG. 6 illustrates the different values. The data shown in FIG. 6 may be subject to various analyses to extract a SVB index representative of the sympathovagal balance of the patient.

Figure 7:
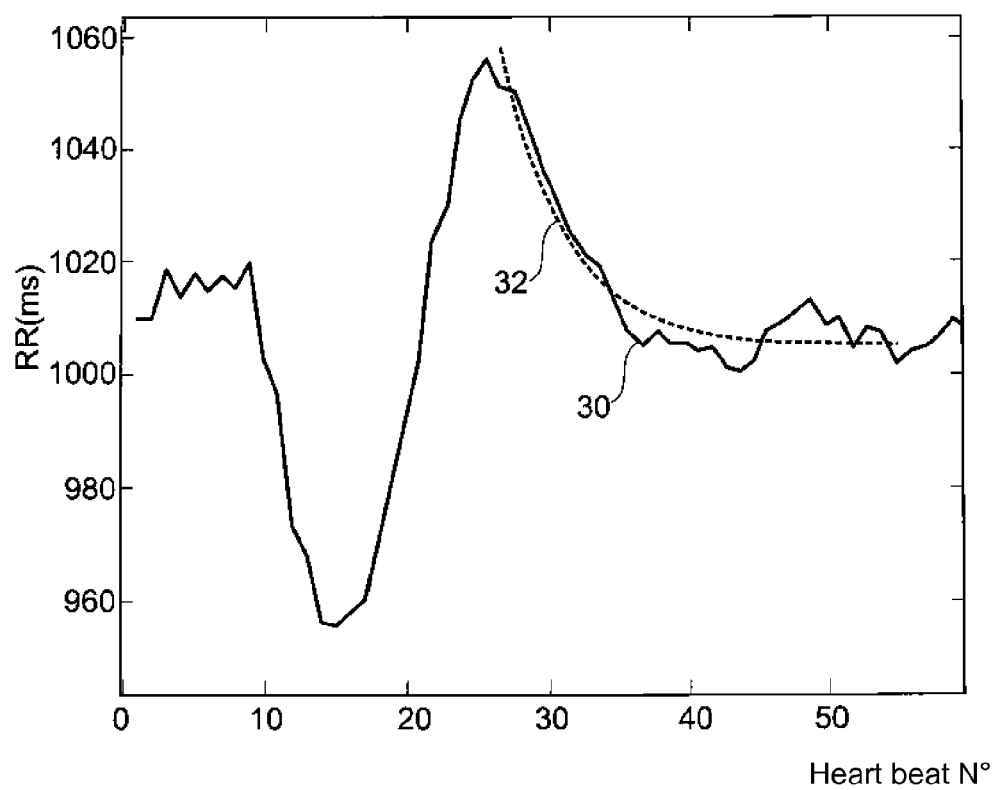
FIG. 7 is an example of a search by analysis of an exponential approximation applied to points derived from heart rate measurement plots during application of the change in autonomic balance, according to an exemplary embodiment.

In the example shown in FIG. 7, the values of the averaged responses are represented according to rank i of the cycle, giving a characteristic 30. To quantify the autonomic response, the device searches for an adjustment of the characteristic 30 by a curve, such as a model 32 (e.g., an exponential model, a polynomial model, etc.). The parameters of the model 32 are then extracted and combined to calculate a representative SVB index. If the model 32 is for example a curve of equation RR=1005.4+65.5786*exp(t/4.6869), to calculate the SVB index the three values {1005.4; 65.5786; 4.6869} are kept.

According to other embodiments, the processing is carried out using indicators derived from an analysis of both the period of delivery of controlled stimulation (ANS) and the recovery period (RÉCUP). The two periods may be described, as noted above, by a succession of four phases #1 to #4: a rapid decrease of the cardiac cycle (RR interval) or increase of a particular parameter of the derivative measurement of endocardial acceleration (phase No. 1), a pseudo-plateau (phase No. 2), rapid increase of the cardiac cycle at the end of the ANS period (phase No. 3), and recovery (phase No. 4).

In one embodiment, a processing method is used to extract from the set of observed values the following indicators:

Slope and peak-to-peak value of the series of values for the phases No. 1 and No. 3, by:

detection and recording of a reference value Ref_Value before the start of the stimulation (from a single measurement or from a locally filtered version of the series);

detection of the maximum value Peak_Value during the stimulation period;

calculation of the absolute value of (Peak_Value−Ref_Value); and adjustment of a linear model between Peak_Value and Ref_Value and calculation of the corresponding coefficients;

Measurement of the duration of the recovery in phases No. 3 and No. 4, as a relative threshold versus Ref_Value or Peak_Value;

Evaluation of the amplitude difference compared to Ref_Value or Peak_Value for N beats after the end of stimulation; and Research of the adjustment of a curve that can be a polynomial, exponential, etc., model, (as discussed above in FIG. 7), the adjustment error then being used as an additional indicator.

These various indicators are then combined with each other to extract a current SVB index, representative of the sympathovagal balance of the patient at a given time.

The invention claimed is:

1. A system for assessing a sympathovagal balance of a patient, comprising:

a generator configured to produce stimulation pulses;

a stimulator that receives the stimulation pulses produced by the generator and outputs a stimulation energy;

a sensor configured to measure a physiological signal; and a processor configured to:

control the generator during a plurality of sequences to produce the stimulation pulses over a test period;

determine a biological parameter of a current activity of the patient derived from the physiological signal, the biological parameter comprising at least one of a PR interval as a dromotropic parameter or an endocardial acceleration as an inotropic parameter;

determine a variation of the biological parameter resulting from the stimulation pulses from at least two values for each sequence of the test period, the at least two values for each sequence including: (i) a base value measured for a baseline period prior to the production of the stimulation pulses; (ii) a current value measured during an ANS period of production of the stimulation pulses; and (iii) a current value measured for a recovery period during which the stimulation pulses are stopped;

wherein the generator produces a plurality of stimulation pulses during the ANS period; and wherein each of the plurality of stimulation pulses includes a rank i, such that the rank i ranges from 1 to n for each sequence; and determine a sympathovagal balance index according to the variation in the biological parameter.

2. The system of claim 1, wherein the physiological signal includes at least one of a cardiac activity, an ECG, a heart rate, breathing, an oxygen saturation, a pulse wave, and a phonocardiogram.

3. The system of claim 1, wherein the processor determines the current value of the biological parameter in synchronization with a cardiac rhythm of the patient during a plurality of successive cardiac cycles during the recovery period.

4. The system of claim 1, wherein each of the plurality of the stimulation pulses corresponds with one of a plurality of samples of the biological parameter, wherein the processor calculates an average of the plurality of samples of the biological parameter of the same rank i over all sequences of the test period, resulting in n averaged values of the biological parameter.

5. The system of claim 4, wherein the n averaged values of the biological parameter are the sympathovagal balance index of the test period, wherein the sympathovagal balance index is calculated during the test period.

6. The system of claim 1, wherein the processor inhibits the generator upon detection of an occurrence of at least one of a heart rate below a predetermined threshold, a presence of a patient's physical activity, a cardiac stimulation delivery, a presence of an apnea or hypopnea episode, and a presence of an arrhythmia episode.

7. A method for assessing a sympathovagal balance of a patient, comprising:

acquiring, by a sensor, a physiological signal;

controlling, by a processor, a generator configured to produce stimulation pulses during a plurality of sequences over a test period;

determining, by the processor, a biological parameter of a current activity of the patient derived from the physiological signal, the biological parameter comprising at least one of a PR interval as a dromotropic parameter or an endocardial acceleration as an inotropic parameter;

determining, by the processor, a variation of the biological parameter resulting from the stimulation pulses from at least two values for each sequence of the test period, the at least two values for each sequence including: (i) a base value measured for a baseline period prior to the production of the stimulation pulses; (ii) a current value measured during an ANS period of production of the stimulation pulses; and (iii) a current value measured for a recovery period during which the stimulation pulses are stopped;

producing, by the generator, a plurality of stimulation pulses during the ANS period, wherein each of the plurality of stimulation pulses includes a rank i, such that the rank i ranges from 1 to n for each sequence; and determining, by the processor, a sympathovagal balance index according to the variation in the biological parameter.

8. The method of claim 7, wherein the physiological signal includes at least one of a cardiac activity, an ECG, a heart rate, breathing, an oxygen saturation, a pulse wave, and a phonocardiogram.

9. The method of claim 7, further comprising determining, by the processor, the current value of the biological parameter in synchronization with a cardiac rhythm of the patient during a plurality of successive cardiac cycles during the recovery period.

10. The method of claim 7, further comprising calculating, by the processor, an average of a plurality of samples of the biological parameter of the same rank i over all sequences of the test period, resulting in n averaged values of the biological parameter, wherein each of the plurality of the stimulation pulses corresponds with one of the plurality of samples of the biological parameter.

11. The method of claim 10, wherein the n averaged values of the biological parameter are the sympathovagal balance index of the test period, wherein the sympathovagal balance index is calculated during the test period.

12. The method of claim 7, further comprising inhibiting, by the processor, the generator upon detection of an occurrence of at least one of a heart rate below a predetermined threshold, a presence of a patient's physical activity, a cardiac stimulation delivery, a presence of an apnea or hypopnea episode, and a presence of an arrhythmia episode.

* * * * *